United States Patent [19]

Kuriyama et al.

[11] Patent Number: 4,507,322

[45] Date of Patent: Mar. 26, 1985

[54] PHARMACEUTICAL COMPOSITION USEFUL FOR IMPROVEMENT AND/OR TREATMENT OF MENTAL SYMPTOMS CAUSED BY ORGANIC DISORDER IN BRAIN

[75] Inventors: Shizuo Kuriyama, Ooi; Mikio Saitoh, Ashiya, both of Japan

[73] Assignees: Eisai Co., Ltd.; Mitsubishi Chemical Industries Limited, both of Tokyo, Japan

[21] Appl. No.: 530,247

[22] Filed: Sep. 8, 1983

[30] Foreign Application Priority Data

Sep. 22, 1982 [JP] Japan .................................. 57-165546

[51] Int. Cl.³ .......................................... A61K 31/135
[52] U.S. Cl. .................................................... 514/648
[58] Field of Search ........................................ 424/330

[56] References Cited

PUBLICATIONS

Chem. Abst., 96–(1982), 210757k.

*Primary Examiner*—Stanley J. Friedman
*Attorney, Agent, or Firm*—Oblon, Fisher, Spivak, McClelland & Maier

[57] ABSTRACT

2-(4-Methylaminobutoxy)diphenylmethane or pharmaceutically acceptable salts thereof have been found to be useful as a pharmaceutical composition for improvement and/or treatment of mental symptoms caused by an organic disorder in the brain.

3 Claims, No Drawings

PHARMACEUTICAL COMPOSITION USEFUL FOR IMPROVEMENT AND/OR TREATMENT OF MENTAL SYMPTOMS CAUSED BY ORGANIC DISORDER IN BRAIN

BACKGROUND OF THE INVENTION

1. Field of the Invention

This invention relates to a pharmaceutical composition useful for improvement and/or treatment of a mental symptom caused by an organic disorder in the brain.

More specifically speaking, the present invention relates to a pharmaceutical composition useful for improvement and/or treatment of mental symptoms caused by an organic disorder in the brain, which composition contains 2-(4-methylaminobutoxy)diphenylmenthane or a pharmaceutically acceptable salt thereof as an active ingredient.

By the term "an organic disorder in the brain" as used herein is meant cerebrovascular diseases caused by morbid cerebral vessels, such as cerebral apoplexy (cerebral infarction and cerebral hemorrhage) and cerebral arteriosclerosis, as well as organic disorders caused by senile dementia, head injury, brain tumor, brain surgery, brain abscess, spinal and cerebellar degenerative symptom, amyotrophic lateral sclerosis, multiple sclerosis, Parkinson disease, chorea, athetosis, hemi-ballism and Wilson disease.

2. Description of the Prior Art

The treatment technique for cerebrovascular disease such as cerebral apoplexy (cerebral infarction and cerebral hemorrhage) and cerebral arteriosclerosis has been developed in recent years in the field of neurosurgery. However, such disease still account for the first or second serious cause for death. In many instances, they are accompanied by mental disorders which remain unchanged over long periods of time. The treatment technique for the above disease are still dissatisfactory even at present, although remarkable progress has already been made in the field of medicine.

A wide variety of symptoms accompanying with patients suffering from cerebrovascular diseases, including subjective symptoms such as headache, heavy feeling in the head, dizziness, tinnitus and hand and foot palsy, neurological symptoms such as speech disturbance, paralysis of upper and/or lower extremities and perceptual disorders, and psychological or psychoneurotic symptoms such as reduced intellectual function such as impaired memory and disturbances in impressibility, reduced spontaneity, emotional disturbances and sleep disturbance. Among these symptoms, the psychological or psychoneurotic symptoms are most difficult to treat. These mental symptoms are said to appear in some forms in about 70% of those patients suffering or suffered from cerebrovascular diseases and have become serious obstacles in treating such patients with a view toward positively having them regain their normal life. If a highly aged man suffers from a cerebrovascular disease, an additional load is applied to his brain whose function has already been lowered due to the aging and the reduction in his mental function is expected to be aggravated further.

When treating cerebrovascular disease internally, a variety of cerebral vasodilators, cerebral metabolite activators and the like has heretofore been employed. These drugs have however brought about almost no improvement to nervous symptoms and mental symptoms although certain improvements have certainly been recognized regarding subjective symptoms.

Furthermore, 1.2% of those over 65 years old are suffering from senile dementia and, due to various mental symptoms caused by senile dementia, tremendous troubles are forced to their family members and other people who look after these patients.

A number of medical investigations has been carried out as to development of these mental symptoms. However, many issues remain still unsolved.

With the foregoing in view, the present inventors have conducted for many years an intensive research on drugs effective for improvement and/or treatment of mental symptoms caused by the above-described organic disorders in the brain. As a result, it has now been found that certain mental symptoms, which have heretofore been difficult to treat, may be clearly improved by administering 2-(4-methylaminobutoxy)diphenylmethane or a pharmaceutically acceptable salt thereof to patients. Symptoms, to which the pharmaceutical composition according this invention may be applied effectively, include not only those caused by the above-described cerebrovascular diseases and senile dementia but also those caused by head injuries, brain surgery, brain tumor, brain abscess, spinal and cerebellar degenerative symptom, amyotrophic lateral sclerosis, multiple sclerosis, Parkinson disease, chorea, athetosis, hemi-ballism and Wilson disease.

SUMMARY OF THE INVENTION

Accordingly, an object of this invention is to provide a novel pharmaceutical composition useful for improvement and/or treatment of a mental symptom caused by an organic disorder in the brain.

In the present invention, illustrative mental symptoms caused by organic disorders in the brain may include reduced spontaneity, impaired intellectual function such as disturbances in impressibility and impaired memory, emotional disturbance, sleep disturbance, etc.

DETAILED DESCRIPTION OF THE PREFERRED EMBODIMENTS 2-(4-Methylaminobutoxy)diphenylmethane useful in the practice of this invention has the following structural formula (I):

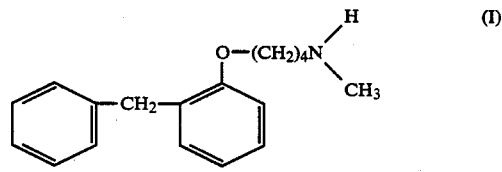

Exemplary of its pharmaceutically acceptable salts are salts of inorganic acids such as hydrochloric acid, hydrobromic acid, hydriodic acid and sulfuric acid; and salts of organic acids such as maleic acid, fumaric acid, succinic acid, acetic acid, malonic acid, citric acid and benzoic acid.

Various processes can be employed for preparing 2-(4-methylaminobutoxy)diphenylmethane. The following process may be given as a representative one.

Namely, the above compound may be obtained by reacting a 2-(ω-halogenobutoxy)diphenylmethane represented by the following general formula (II):

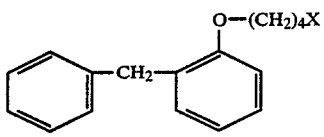

wherein X is halogen atom, with methylamine.

The reaction conditions will be explained more in detail below. Methylamine are used in an amount of 1–100 moles per mole of the 2-(ω-halogenobutoxy)diphenylmethane. The reaction rate can be enhanced by using the excess amine.

The reaction can be carried out without an added solvent. However, the use of a reaction-inert solvent makes a homogeneous reaction possible. Such solvents include water, dioxane, tetrahydrofuran, dimethylsulfoxide, a lower alcohol and the mixture thereof. The reaction temperature is not critical, but normally ranges from room temperature to 150° C. The reaction time varies widely with the reaction temperature and the reactivity of the starting materials, but normally is in the range of from 10 minutes to 40 hours.

The presence of bases which neutralize a hydrogen halide formed in the course of the reaction accelerates the reaction. Examples of such bases are inorganic bases such as potassium hydroxide, sodium hydroxide, potassium carbonate, sodium carbonate and the like; and tertiary amines such as pyridine, triethylamine and the like. The amount of the base to be employed is normally in the range of 1–5 moles per mole of the 2-(ω-halogenobutoxy)diphenylmethane.

When the base is absent 2-(4-aminobutoxy)diphenylmethane reacts with a hydrogen halide formed during the reaction, and are converted into the acid addition salts thereof. In order to obtain a desired acid addition salt, it is necessary first to drive off the excess methylamine and the solvent and then to add a strongly basic aqueous solution such as an aqueous KOH or NaOH solution to the residue so as to convert the acid addition salt of 2-(4-methylaminobutoxy)diphenylmethane to free 2-(4-methylaminobutoxy)diphenylmethane, followed by its extraction with a solvent such as ethyl ether, chloroform or benzene. By adding the desired acid further to the extract to neutralize it, the intended acid addition salt of 2-(4-methylaminobutoxy)diphenylmethane can be obtained. 2-(4-methylaminobutoxy)diphenylmethane or its acid addition salt, obtained in the above reaction, may be purified by recrystallizing it from a suitable solvent such as an alcohol, ether or the like.

The results of some clinical tests will next be described in order to demonstrate the effects of this invention in detail.

Clinical Case 1

42-Year-Old-Male, Cerebral Hemorrhage

Before administration, the conditions of the patient were as follows:

He suddenly lost consciousness while he was working, and then developed left hemi-paralysis. After admitted in the hospital, his unconsciousness remained for several days. Thereafter, his consciousness level was almost normalized and the left hemi-paralysis changed gradually from flaccid hemi-paralysis to spastic hemi-paralysis. From an elapsed time of about 2 months, he proceeded with rehabilitation for 9 months. As a result, he was able to walk with the aid of a cane and leg gears. However, his left arm became useless due to disuse and left spastic hemi-paralysis, reflex exacerbation at right arm and leg and dysarthria were observed. He also developed further symptoms such as low positiveness, lowered interests to surroundings, silence and iron and gloomy face. A CT diagnosis indicated a low absorption region, which seemed to be attributed to a medium degree of outer cerebral hemorrhage, in a right shell portion.

2-(4-Methylaminobutoxy)diphenylmethane hydrochloride was administered orally at the dosage of 75 mg per day to the above patient. From about the second week after the initiation of the administration, he started looking more cheerful and became more responsive when spoken to. After an elapsed time of 4 weeks, his spontaneity and positiveness were improved further and he was able to come to the hospital by himself although his wife's attendance had previously been indispensable. His left hemi-paralysis and dysarthria were unchanged and no side effect was observed at all. No change was recognized in a laboratory test.

Clinical Case 2

70-Year-Old-Male, Cerebral Infarction (Cerebral Thrombosis)

Before the administration, the conditions of the patient were as follows:

The patient suffered from left incomplete hemiparalysis and, although his muscular strength was almost normal, his muscle tonus was rigidospastio and pathologic reflex was observed at both sides. His impressibility, memory and calculation capacity were all lowered to medium levels. He was expressionless and developed emotional incontinence. From time to time, he did violence to helpers and his family members when he was unhappy or dissatisfied. This was however not the case when he confronted physicians and he took their medical examinations calmly. His spontaneity was low. He did neither watch TV nor read newspapers too much. He seldom went out for a walk. A CT diagnosis indicated, in addition to right basal nucleus, some scattered low absorption regions which seemed to correspond to small infarcts and a medium degree of atrophy in the frontal lobe. Various drugs were used but the above-mentioned symptoms were not improved and, on the contrary, were rather aggravated. Nocturnal delirium was developed from time to time and urinary incontinence was developed frequently.

He was then administered with 2-(4-methylaminobutoxy)diphenylmethane hydrochloride, which is the compound useful in the practice of this invention, at the dosage of 150 mg per day by the oral route. His facial appearance then became more cheerful and he became more cheerful also internally. His violence decreased and he tended to go out more positively for a walk. In addition, his nocturnal delirium decreased and no urinary incontinence was developed any longer. No change was recognized in a laboratory test.

Clinical Case 3

74-Year-Old-Female, Cerebral Infarction (Cerebral Thrombosis)

Before the administration, the conditions of the patient were as follows:

The patient developed left hemi-paralysis three years preceding the administration, but her paralysis was of a light level. She was able to walk by herself. She did not lose consciousness when the left hemi-paralysis was developed. However, taking the development of the left hemi-paralysis as a turning point her spontaneity and impressibility were lowered gradually. Thereafter, her right arm became difficult to hold chopsticks and her dysarthria became easier to notice. She was not motivated to watch TV too much and lack of spontaneity was clearly observed. In contrast with this, she was unable to control herself whenever she had something wanted to do, for example, there was something to eat and ignored suggestions from her family members to wait for a while, and was thus excited. Namely, she developed considerable emotional incontinence.

When 2-(4-methylaminobutoxy)diphenylmethane hydrochloride, a compound according to this invention, was administered at the dosage of 150 mg per day to her, her spontaneity was started to get better 2 weeks later as she had more conversation and walking and started to watch TV with her family members. This trend of recovery became clearer from the 4th week and her facial appearance became cheerful and active. Her emotional incontinence was also improved to a relatively large extent. Her neurological symptoms were not changed too much, but she did not feel heavy in her head any longer. No side effects were observed at all, including a laboratory test.

Clinical Case 4

47-Year-Old-Male, Cerebral Infarction, (Cerebral Thrombosis)

He developed the above disease about 1 year and 5 months before the administration. He had left hemi-paralysis and anarthria from the beginning. A CT diagnosis, which was conducted at the time of the administration, indicated a low absorption region in contact to the front corner of the right ventricle of brain and a cerebral angiogram proved the presence of an occlusion at the right internal carotid artery. The dyskinesia of his left arm and leg was of the medium degree and he was able to walk with an aid of a cane. He, however, showed a reduction in positiveness. The patient was orally administered with 2-(4-methylaminobutoxy)diphenylmethane hydrochloride at the dosage of 75 mg per day. The results after an elapsed time of 8 weeks indicated improvements to the interests to TV, books and the like and to the hypobulia for rehabilitation and walking in spontaneity and further improvements to disturbances in impressibility and dyscalculia in intellectual function as well as still further improvements to poor expression in emotion. However, no improvements were observed with respect to dysarthria and left hemi-paralysis. Incidentally, no side effects were observed at all, including a clinical test.

Clinical Case 5

58-Year-Old-Male, Cerebral Infarction (Cerebral Thrombosis)

The disease was developed about 10 days before his admission to the hospital. He then suddenly developed right hemi-paralysis, dysarthria and emotional incontinence. A CT diagnosis, which was made at the time of his admission, indicated cerebral atrophy but no apparent low absorption region was observed. A cerebral angiogram showed considerable constriction in the horizontal portions of left mesencephalic and cerebral arteries and an incomplete wall in the syphone portion of the left internal carotid artery. Subsequent to his admission to the hospital, γ-aminolactic acid and Pentoxifylline were administered. Some improvements were observed to the symptoms but his spontaneity and emotional incontinence were hardly improved. Accordingly, from the 40th day after his admission to the hospital, 2-(4-methylaminobutoxy)diphenylmethane hydrochloride was orally administered at the dosage of 150 mg per day. After an elapsed time of 3.8 weeks, his reaction was somewhat improved in spontaneity when spoken to or greeted. His interests to TV and books as well as to rehabilitation and walking were improved. In his emotion, some improvements were recognized with respect to emotional incontinence and incompetence in interpersonal situation. It is also worthy to note that an improvement to the right hemi-paralysis was also recognized. No side effects were developed a laboratory test did not contain any abnormality.

Clinical Case 6

78-Year-Old-Male (Senile Dementia)

The patient started to show reduction in impressibility and memory from about 3 years preceding the administration. A CT diagnosis found cerebral atrophy throughout the brain but no cerebrovascular disease was recognized. However, he showed symptoms of typical senile dementia, including development of lowered intellectual function such as poor imagination and declined impressibility and memory.

When 2-(4-methylaminobutoxy)diphenylmethane hydrochloride was administered by the oral route at the dosage of 150 mg per day, he was improved in emotion and looked easier to deal with and more cheerful. In addition, it is worthy to mention that he did not develop urinary incontinence any longer. No side effects were developed and a laboratory test did not contain any abnormality.

Clinical Case 7

72-Year-Old-Male (Senile Dementia)

The patient started to develop from about 3 years preceding the administration, impaired memory, reduced spontaneity, emotional disturbance, hyperkinesia and wandering. A CT diagnosis indicated senile dementia which was accompanied by extensive cerebral atrophy. This patient was orally administered at the dosage of 150 mg per day with 2-(4-methylaminobutoxy)diphenylmethane hydrochloride. After an elapsed time of 2 weeks from the initiation of the administration, he started to show spontaneity and became more competent in interpersonal situation. No side effects were developed and no abnormality was contained in a laboratory test.

Next, results of an acute toxicity test ($LD_{50}$ mg/kg) of the compound of this invention will be shown in Table 1.

TABLE 1

|  |  | per oral | Subcutaneous injection | Intramuscular injection | Intravenous injection |
|---|---|---|---|---|---|
| rat (Wistar) | ♂ | 1440 | 256 | 246 | 42 |
|  | ♀ | 1414 | 262 | 246 | 37 |
| rat (Fischer) | ♂ | 1494 | 306 | 427 | 41 |
|  | ♀ | 1607 | 358 | 346 | 47 |
| Mouse (dd) | ♂ | 761 | 342 | 375 | 45 |
|  | ♀ | 833 | 327 | 375 | 45 |

As apparent from Table 1, it is appreciated that the compound useful in the practice of this invention is a drug having a high level of safety.

As readily appreciated from the above clinical cases, it has been found that the present invention is effective for improving and/or treating various mental symptoms caused by organic disorders which are in turn accompanied by cerebrovascular diseases, senile dementia, head injury, brain surgery, brain tumor, brain abscess, spinal and cerebellar degenerative symptom, amyotrophic lateral sclerosis, multiple sclerosis, Parkinson disease, chorea, athetosis, hemi-ballism, Wilson disease, etc. The compound useful in the practice of this invention has extremely low toxicity and enjoys a high degree of safety. Although it is unavoidably necessary to continue the administration over a long period of time due to the nature of the above diseases, the compound useful in the practice of this invention permits its continuous administration over a long period of time. Here again, the present invention is believed to be extremely valuable.

When using the compound of this invention as a pharmaceutical preparation useful for improvement and/or treatment of a mental symptom caused by an organic disorder in the brain, it may be administered by the oral or parenteral route (intramuscular, subcutaneous or intravenous administration, or the like). The dosage varies depending on the type of each disease, the degree of each symptom, the age of each patient, his or her weight, the kind of concurrent treatment if any, the nature of desired effects, etc. The dosage is thus not limited to any specific range but may generally be from about 5 mg to about 300 mg and, preferably, from about 50 mg to 200 mg per day for an adult.

In order to form the compound of this invention into a dosable preparation, it may be formed into such preparations as tablets, granular preparations, powders, capsules, injectable preparations, suppositories, etc. in accordance with methods commonly employed in the technical field of formation into dosable preparations.

Namely, when forming solid preparations for oral administration, the main ingredient is added with an excipient and, if necessary, a binder, disintegrator, lubricant, colorant, flavoring agent, etc. and the resulting mixture is then formed into tablets, coated tablets, granules, powders, capsules and the like.

Illustrative of such excipients, are lactose, corn starch, white sugar, glucose, sorbit, crystalline cellulose, etc. Examples of such binders include polyvinyl alcohol, polyvinyl ether, ethyl cellulose, methyl cellulose, gum arabic, tragacanth, gelatin, shellac, hydroxypropyl cellulose, hydroxypropyl starch, polyvinylpyrrolidone, and the like. Examples of disintegrators are starch, agar, gelatin powder, crystalline cellulose, calcium carbonate, sodium hydrogen-carbonate, calcium citrate, dextrin, pectin, and the like. Exemplary of such lubricants are magnesium stearate, talc, polyethylene glycol, silica, hardened vegetable oil, etc. Any colorants may be used so long as they are permitted to be added to pharmaceutical products. Representative of such flavoring agents are cacao powder, menthol, aromatic acid, peppermint oil, borneol, cassia powder, and the like. Needless to say, these tablets and granular preparations be applied with sugar coatings, gelatin coatings, or any suitable coatings as needed.

When forming an injectable preparation, the main ingredient is first added with a pH-adjusting agent, buffer, stabilizer, preservative, etc. and then formed into a subcutaneously, intramuscularly or intravenously injectable preparation. The compound of this invention has very high level of safety as mentioned above. This is extremely important as the continual administration of a medicine over a long period of time is indispensable for the compound of this invention to bring out its pharmacological effects.

Certain Production and Preparation Examples, which pertain to the present invention, will next be described.

Production Example 5.0 g (0.016 mole) of 2-(4-bromobutoxy)diphenylmethane was dissolved in a mixture of 100 ml of ethanol and 20 ml of a 40% aqueous solution of methylamine. After allowing the resultant solution to stand at room temperature for 8 hours, ethanol and excess methylamine were removed under reduced pressures. A 2N-aqueous solution of sodium hydroxide was added to the thus-obtained oily substance, followed by extraction with ethyl ether.

Ethyl ether was then evaporated to obtain a syrupy and oily substance, to which 2N-HCl was added. The resultant mixture was evaporated under reduced pressures, thereby obtaining 2-(4-methylaminobutoxy)diphenylmethane hydrochloride. It was recrystallized from a mixed solvent of ethanol and ethyl ether.

Yield: 4.7 g (96%).
Melting point: 114°–119° C.
Elemental analysis: for $C_{18}H_{23}NO \cdot HCl$

|  | C (%) | H (%) | N (%) |
|---|---|---|---|
| Calculated | 70.68 | 7.91 | 4.58 |
| Found | 70.93 | 7.99 | 4.35 |

Preparation Example 1: (Capsules)

| | |
|---|---|
| 2-(4-methylaminobutoxy)-diphenylmethane.HCl | 100 g |
| Mannitol | 300 g |
| Corn starch | 450 g |
| Milk sugar | 300 g |
| Hydroxypropyl cellulose | 38 g |
| Calcium stearate | 12 g |

The above components were mixed and formed into capsules, each of 120 mg, in a manner known per se in the art.

Preparation Example 2: (Tablets)

| | |
|---|---|
| 2-(4-methylaminobutoxy)-diphenylmethane.HCl | 100 g |
| Corn starch | 200 g |
| Milk sugar | 500 g |
| Calcium carboxymethylcellulose | 150 g |
| Polyvinyl pyrrolidone | 75 g |
| Talc | 75 g |
| Microcrystalline cellulose | 250 g |

The above components were mixed, granulated and then compression-formed into tablets, each being 120 mg heavy, in a manner known per se in the art.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method for improving and/or treating a patient afflicted with a mental symptom caused by a cerebrovascular disease or senile dementia in the brain, which comprises:
    administering to said patient a therapeutically effective amount of 2-(4-methylaminobutoxy)diphenylmethane or a pharmaceutically acceptable salt thereof as an active ingredient in combination with a pharmaceutically acceptable carrier.

2. A method according to claim 1, wherein the organic disorder in the brain is a cerebrovascular disease.

3. A method according to claim 1, wherein the organic disorder in the brain is senile dementia.

* * * * *